US00PP15570P2

(12) United States Plant Patent
Olesen et al.

(10) Patent No.: US PP15,570 P2
(45) Date of Patent: Feb. 15, 2005

(54) ROSE PLANT NAMED 'POULAC012'

(50) Latin Name: *Rosa hybrida*
Varietal Denomination: POULAC012

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/812,713

(22) Filed: Mar. 29, 2004

(51) Int. Cl.[7] ..... A01H 5/00
(52) U.S. Cl. ..... Plt./150
(58) Field of Search ..... Plt./150, 149, 108

*Primary Examiner*—Anne Marie Grunberg
*Assistant Examiner*—June Hwu

(57) ABSTRACT

A new garden rose plant of the compact floribunda class which has abundant, red flowers and attractive foliage. This new and distinct variety has shown to be uniform and stable in the resulting generations from asexual propagation.

2 Drawing Sheets

Botanical classification: *Rosa hybrida.*
Variety denomination: 'POULac012'.

SUMMARY OF THE INVENTION

The present invention constitutes a new and distinct variety of garden rose plant which originated from a controlled crossing between the female parent, an unnamed seedling, and the non-patented male parent plant named 'Emotion'. The two parents were crossed during the summer of 1993 and the resulting seeds were planted in a controlled environment in Fredensborg, Denmark. The new variety is named 'POULac012'.

The new variety may be distinguished from its female seed parent by the following combination of characteristics:

1. While the seed parent has salmon colored flowers, 'POULac012' has Red Group 42A flowers.
2. While the seed parent has an average height of 100 cm, 'POULac012' is more compact, growing 40 to 60 cm in height.

The new variety may be distinguished from its unnamed male pollen parent 'Emotion', by the following combination of characteristics:

1. While the pollen parent has pink flowers, 'POULac012' has Red Group 42A flowers.
2. While the pollen parent has a tall growth habit, 'POULac012' is compact.

The objective of the hybridization of this rose variety was to create a new and distinct variety for garden use with unique qualities, such as:

1. Uniform and abundant red flowers which do not fade;
2. Vigorous, compact growth when propagated both as a budded rose and on its own roots;
3. Disease resistance.

This combination of qualities is not present in previously available commercial cultivars of this type, known to the inventors, and distinguish 'POULac012' from all other varieties of which we are aware.

As part of their rose development program, L. Pernille Olesen and Mogens N. Olesen germinated the seeds from the aforementioned hybridization during winter of 1993 and conducted evaluations on the resulting seedlings in a controlled environment in Fredensborg, Denmark.

'POULac012' was selected in the spring 1994 by the inventors as a single plant from the progeny of the aforementioned hybridization.

Asexual reproduction of 'POULac012' by traditional budding and rooted cuttings was first done by L. Pernille and Mogens N. Olesen in their nursery in Fredensborg, Denmark in July, 1994. This initial and other subsequent asexual propagations conducted in controlled environments have demonstrated that the characteristics of 'POULac012' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems, of 'POULac012'. Specifically illustrated in SHEET 1:

FIG. 1.1; Open flower, stem showing cluster of open flowers, branching, and the attachment of leaves, buds, and peduncles;

FIG. 1.2; Flower petals, detached;

FIG. 1.3; Sepals, receptacle, and peduncle;

FIG. 1.4; Flower bud closed, flower bud as sepals unfold, and partially open.

Specifically illustrated in SHEET 2:

FIG. 2.1; Leaves;

FIG. 2.2. Bare stem exhibiting thorns.

DETAILED DESCRIPTION OF THE VARIETY

The following is a description of 'POULac012', as observed in its growth in a field nursery in Jackson County, Oreg. Observed plants are grown on *Rosa multiflora* understock and are 3 years of age. Color references are made using The Royal Horticultural Society (London, England) Colour Chart, 1995, except where common terms of color are used.

For a comparison, several physical characteristics of the rose variety 'POULsail', a rose variety from the same inventors described and illustrated in U.S. Plant Pat. No. 11,501 issued Sep. 5, 2000, are compared to 'POULac012' in Chart 1.

CHART 1

| | 'POULac012' | 'POULsail' |
|---|---|---|
| Upper surface, outer petals, after opening | Red Group 42A | Red Group 41C |
| Petalage | 30 to 35 petals | 40 to 45 petals |
| Flower Diameter | 50 mm | 65 to 75 mm |

FLOWER AND FLOWER BUD

Blooming habit: Continuous.

Flower bud:

*Size.*—Upon opening, 28 mm in length from base of receptacle to end of bud. Bud diameter is 10 mm.

*Bud form.*—Long, pointed ovoid.

*Bud color.*—As sepals unfold, petals are Red Group 45A.

*Sepals.*—Upper Surface: Color: Green Group 139D. Pubescence: Medium. Lower Surface: Color: Yellow-Green Group 144A with anthocyanic intonations of Greyed-Purple Group 185A. Texture: Smooth with few stipitate glands. Sepal Shape: Sepal apex is cirrhose. Base is flat at union with receptacle. Sepal Margin: Margins have weak foliaceous appendages on three of the five sepals. Size: 23 mm(l)×8 mm(w).

*Receptacle.*—Surface Texture: Smooth and glabrous. Shape: Urn-shaped. Size: 8 mm (h)×7 mm (w). Color: Yellow-Green Group 144A with anthocyanic intonations of Greyed-Purple Group 185A.

*Peduncle.*—Surface: Glabrous with few stipitate glands and prickles. Length: 35 to 40 mm. Color: Yellow-Green Group 144B with anthocyanic intonations of Greyed-Purple Group 185A. Strength: Somewhat strong.

*Borne.*—In clusters of 5 to 11 flower buds per stem.

Flower bloom:

*Fragrance.*—Very light floral scent.

*Duration.*—The blooms have a duration on the plant of approximately 10 to 14 days. Petals fall cleanly away from plant.

*Size.*—Flower diameter is 50 mm when open. Flower depth is 23 mm on average.

*Form.*—General: Rosette. Very-double flowers with many slightly overlapping petals. Shape of flower when viewed from the side: Upon opening, upper part: Flat. Upon opening, lower part: Concave. Open flower, upper part: Flattened convex. Open flower, lower part: Concave.

Petalage: 30 to 35 petals under normal conditions with 9 petaloids.

Color:

Upon opening, petals:

*Outermost petals.*—Outer side: Red Group 53C to Red-Purple Group 61C. Inner Side: Red Group 42A.

*Innermost petals.*—Outer side: Red Group 53C to Red-Purple Group 61C. Inner Side: Red Group 42A.

Upon opening, basal petal spots:

*Outermost petals.*—Outer side: White Group 157A. Inner Side: White Group 157A.

*Innermost petals.*—Outer side: White Group 157A. Inner Side: White Group 157A.

After opening, petals:

*Outermost petals.*—Outer side: Red Group 53C to Red-Purple Group 61C. Inner Side: Red Group 42A.

*Innermost petals.*—Outer side: Red Group 53C to Red-Purple Group 61C. Inner Side: Red Group 42A.

After opening, basal petal spots:

*Outermost petals.*—Outer side: White Group 157A. Inner Side: White Group 157A.

*Innermost petals.*—Outer side: White Group 157A. Inner Side: White Group 157A.

General tonality: On open flower Red Group 42A. No change in the general tonality at the end of the 7th day. Afterwards, general tonality is Red Group 42A with intonations of Red-Purple Group 61C.

Petals:

*Petal reflex.*—None.

*Margin.*—Entire and uniform. Undulations of margin are absent to weak.

*Shape.*—Apex: Round. Base: Acute.

*Size.*—23 to 30 mm (l)×20 to 32 mm (w).

*Texture.*—Smooth.

*Thickness.*—Thin.

*Arrangement.*—Not Formal.

Petaloids:

*Quantity.*—7 to 9.

*Color.*—Red Group 53C to Red-Purple Group 61C.

*Size.*—21 mm (l)×12 mm (w).

*Shape.*—Somewhat irregular. Base is acute. Apex is rounded.

Reproductive organs:

*Pistils.*—Length: 7 mm. Quantity: 21.

*Pollen.*—None observed.

*Anthers.*—Size: 2 mm in length. Color: Greyed-Orange Group 163B. Quantity: 43 (actual count).

*Filaments.*—Color: Yellow Group 2D. Length: 5 mm.

*Stigmas.*—Superior to relative to the length of filaments and the height of the anthers. Colors: Greyed-Yellow Group 162D.

*Styles.*—Color: Greyed-Yellow Group 162D. Other Intonations: Weak intonations of Red-Purple Group 63B.

*Hips.*—None Observed in the field nursery in Jackson County Oreg.

PLANT

Plant growth: Moderate, upright to bushy. When grown as a budded field grown plant on *Rosa multiflora* understock, the average height of the plant is 40 to 60 cm and the average width is 40 cm.

Stems:

*Color.*—Young wood: Yellow-Green Group 144B. Older wood: Yellow-Green Group 144B.

*Surface texture.*—Young wood: Smooth. Older wood: Smooth.

Thorns:

*Incidence.*—12 thorns per 10 cm of stem.

*Size.*—Average length: 7 mm.

*Color.*—Greyed-Purple Group 183A.

*Shape.*—Deeply concave.

Plant foliage: Normal number of leaflets on normal leaves in middle of the stem: 7 leaflets.

*Compound leaf size.*—110 mm in length by 70 mm wide.

*Quantity.*—Average.

*Color.*—Mature Foliage: Upper surface is: Green Group 137B. Lower surface is: Green Group 138B.

Juvenile foliage: Upper surface is: Green Group 137B. Lower surface is: Green Group 138B.

Plant leaves and leaflets:

*Stipules.*—Size: 12 mm in length. Quantity: 2 per compound leaf. Margins: Finely serrated with stipitate glands. Color: Yellow-Green Group 144A.

*Petiole.*—Length: 20 mm. Above: Color: Yellow-Green Group 144B to 144C. Anthocyanic intonations the color of Greyed-Purple Group 185A observed. Underneath: Spines.

*Rachis.*—Underneath: Spines. Color: Yellow-Green Group 144B to 144C with anthocyanic intonations of Greyed-Purple Group 185A on the upper side. Length: 55 mm.

*Leaflet.*—Size: 35 to 55 mm (l)×28 to 40 mm (w). Edge: Serrated. Shape: Generally ovate. Base is round. Leaflet apex is cuspidate. Texture: Smooth. Thickness: Thick. Arrangement: Odd pinnate. Venation: Reticulate. Glossiness: Moderate Glossy.

Disease resistance: Above average resistance to mildew, rust, black spot, and Botrytis under normal growing conditions in Jackson County, Oreg.

Cold hardiness: The variety 'POULac012' has been found to be cold tolerant to USDA Cold Hardiness Zone 6.

It is claimed:

1. A new and distinct variety of rose plant of the compact floribunda rose class, substantially as herein illustrated and described as a distinct and novel rose variety due to its abundant red flowers, disease resistance, and extended period of bloom.

* * * * *

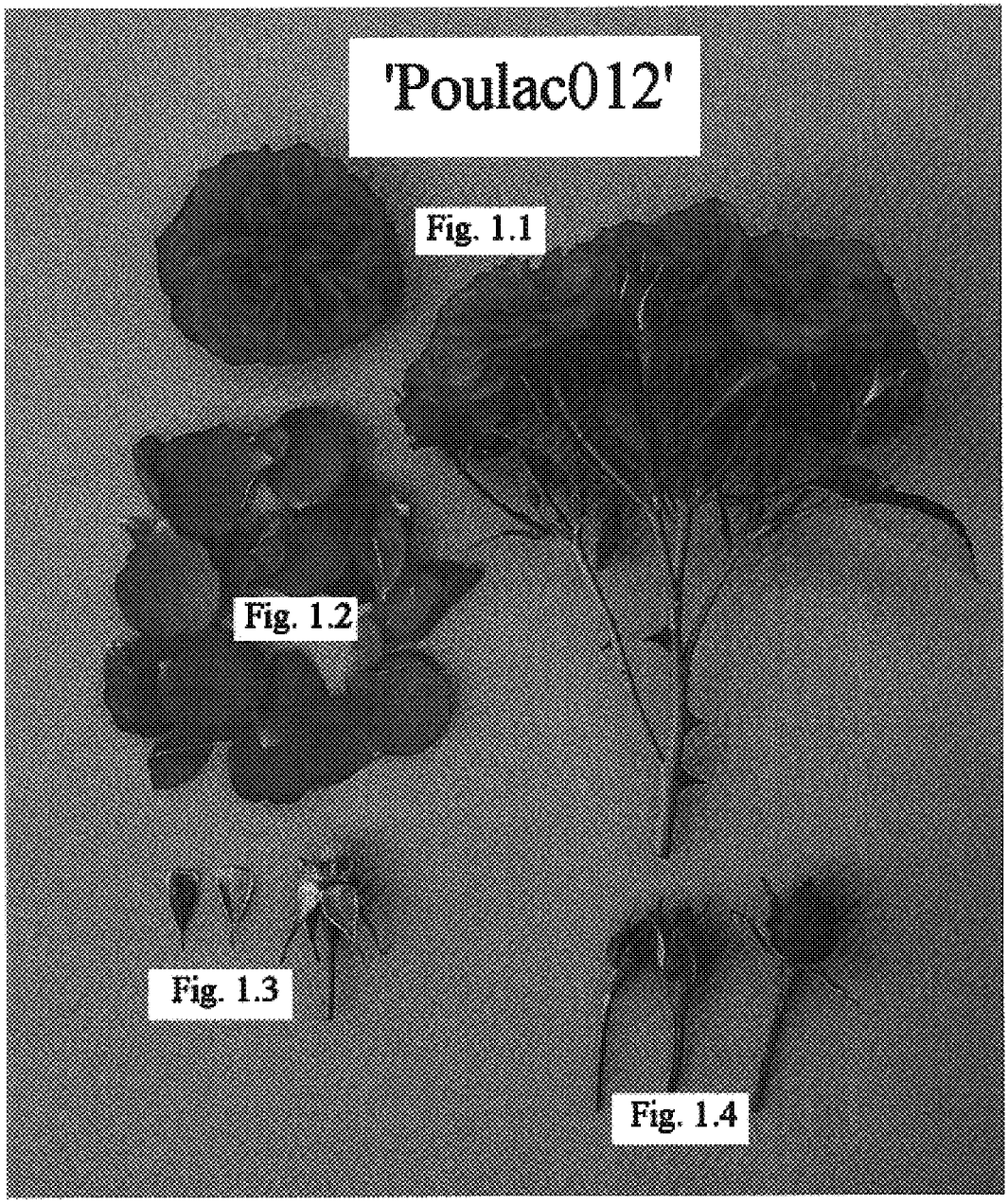
'Poulac012'
Fig. 1.1
Fig. 1.2
Fig. 1.3
Fig. 1.4

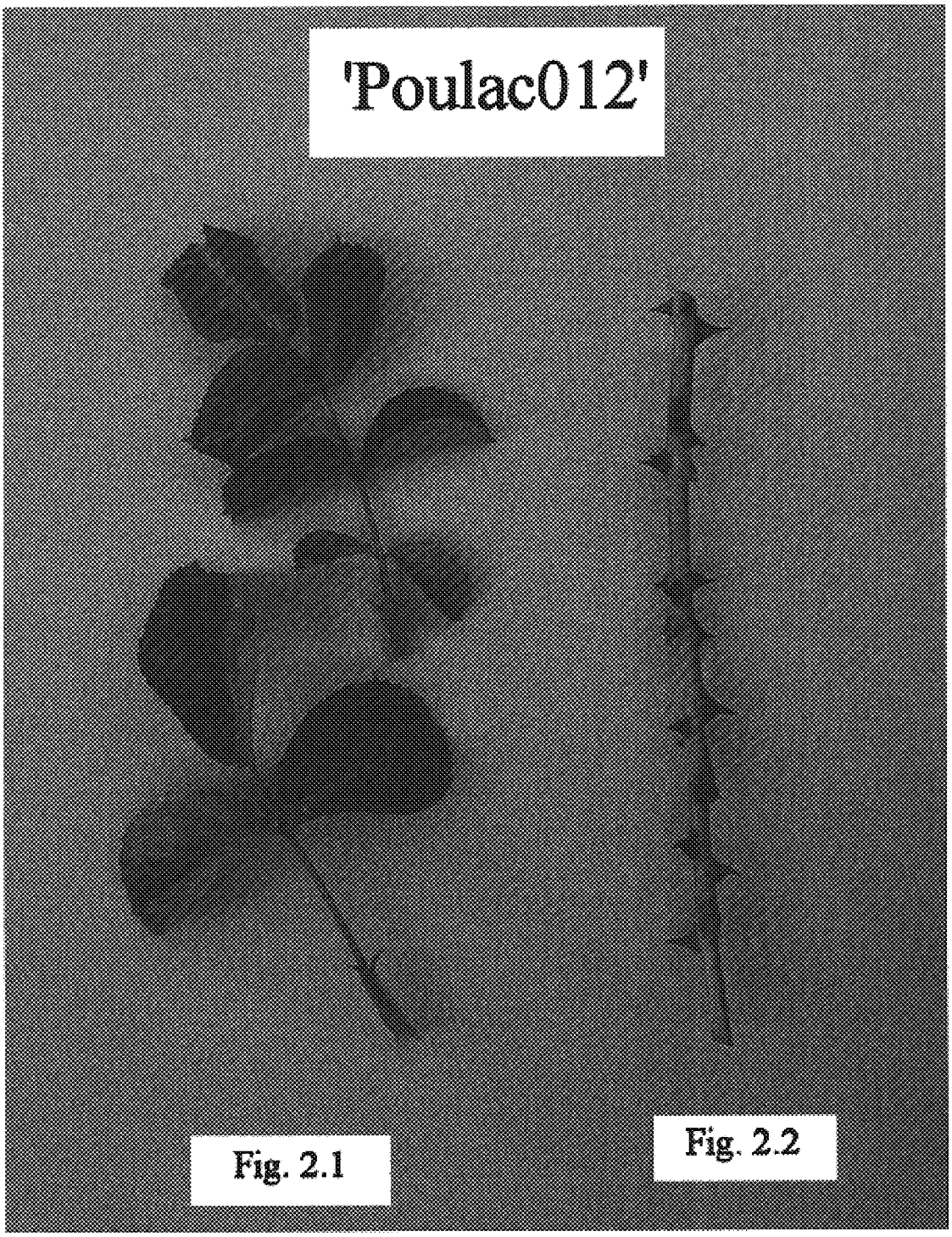
Fig. 2.1
Fig. 2.2